United States Patent [19]

Muller et al.

[11] 4,315,987

[45] Feb. 16, 1982

[54] CONTINUOUS FERMENTATION PROCESS

[75] Inventors: Werner C. Muller, Dobbs Ferry, N.Y.; Franklyn D. Miller, Cincinnati, Ohio

[73] Assignee: National Distillers & Chemical Corp., New York, N.Y.

[21] Appl. No.: 129,516

[22] Filed: Mar. 12, 1980

[51] Int. Cl.³ .............................................. C12P 7/14
[52] U.S. Cl. .................................. 435/162; 435/941; 435/942
[58] Field of Search ............................... 435/161, 162

[56] References Cited

U.S. PATENT DOCUMENTS 2,419,960  5/1947  Legg .................................... 435/162
2,431,004 11/1947  Wickerham ..................... 435/162 X

OTHER PUBLICATIONS

Cysewski et al., Biotechnology and Bioengineering, vol. XX, pp. 1421–1444 (1978).
White, Yeast Technology, 1954, pp. 334–337.

Primary Examiner—Lionel M. Shapiro
Attorney, Agent, or Firm—Kenneth D. Tremain

[57] ABSTRACT

A fermentable sugar feed containing fermentable sugar oligomers is continuously converted by fermentation to dilute aqueous ethanol ("beer") in a series of agitated fermentation vessels employing at least two strains of yeast, one of which provides a relatively high rate of conversion of fermentable sugar to ethanol and the other of which provides a relatively high rate of conversion of fermentable sugar oligomer to ethanol.

9 Claims, 1 Drawing Figure

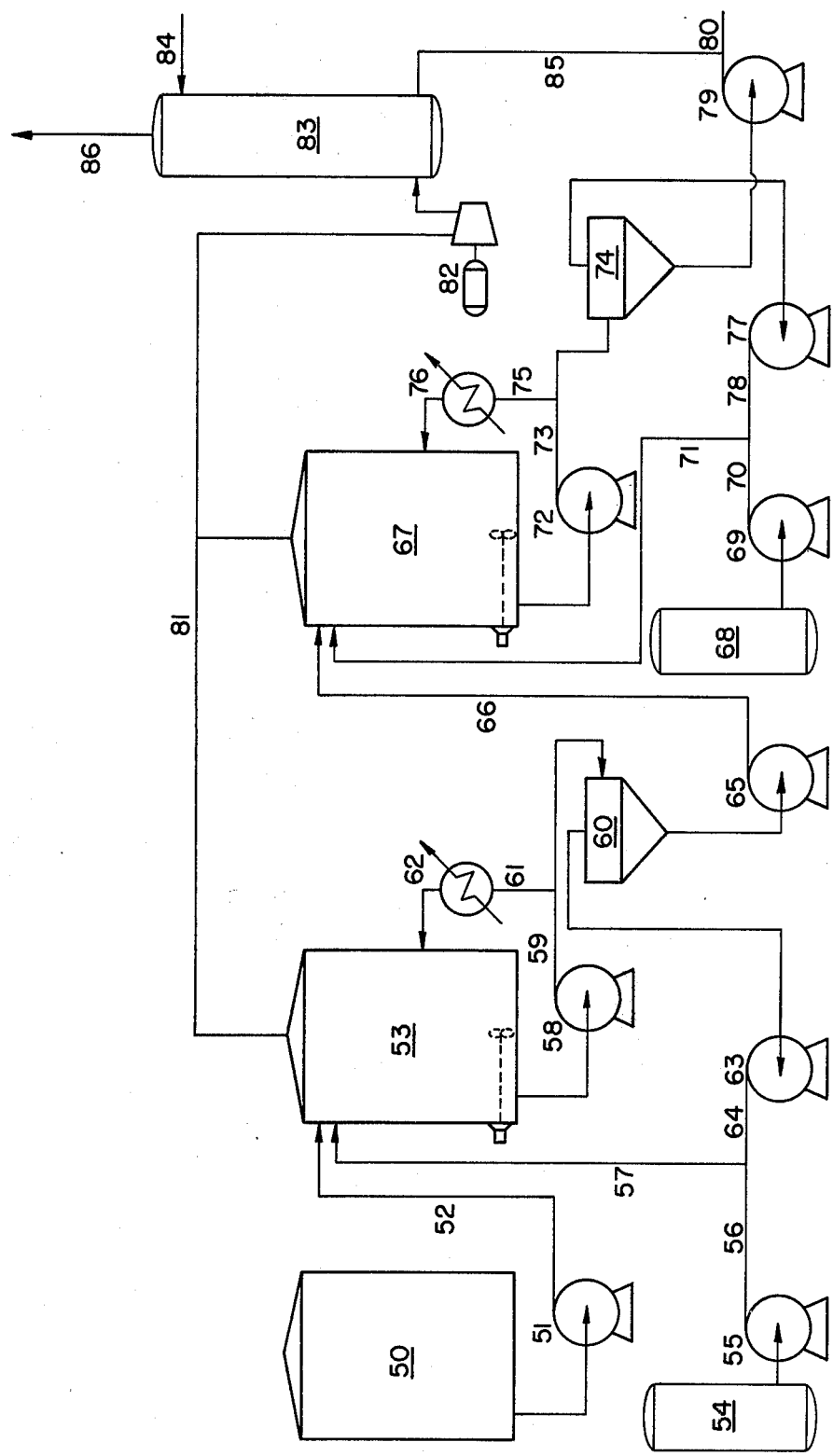

CONTINUOUS FERMENTATION PROCESS

BACKGROUND OF THE INVENTION

1. Field of the Invention

This invention relates to processes for the manufacture of ethanol by continuous fermentation.

2. Description of the Prior Art

With the ever-increasing depletion of economically recoverable petroleum reserves, the production of ethanol from vegetative sources as a partial or complete replacement for conventional fossil-based liquid fuels becomes more attractive. The substitution of ethanol for at least a portion of petroleum based fuels is particularly critical for developing economies where proven domestic petroleum reserves are limited. In some areas, the economic and technical feasibility of using a 90% unleaded gasoline-10% anhydrous ethanol blend ("gasohol") has shown encouraging results. According to a recent study, gasohol powered automobiles have averaged a 5% reduction in fuel compared to unleaded gasoline powered vehicles and have emitted one-third less carbon monoxide than the latter. In addition to offering promise as a practical and efficient fuel, biomass-derived ethanol in large quantities and at a competitive price has the potential in some areas for replacing certain petroleum-based chemical feedstocks. Thus, for example, ethanol can be catalytically dehydrated to ethylene, one of the most important of all chemical raw materials both in terms of quantity and versatility.

The various operations in processes for obtaining ethanol from such recurring sources as cellulose, cane sugar, amylaceous grains and tubers, e.g., the separation of starch granules from non-carbohydrate plant matter and other extraneous substances, the chemical and/or enzymatic hydrolysis of starch to fermentable sugar (liquefaction and saccharification), the fermentation of sugar to a dilute solution of ethanol ("beer") and the recovery of anhydrous ethanol by distillation, have been modified in numerous ways to achieve improvements in product yield, production rates and so forth. For ethanol to realize its vast potential as a partial or total substitute for petroleum fuels or as a substitute chemical feedstock, it is necessary that the manufacturing process be as efficient in the use of raw materials as possible so as to maximize the amount of product produced per unit of carbohydrate feed and thereby enhance the standing of the ethanol as an economically viable replacement for petroleum based raw materials. To date, however, relatively little concern has been given to optimizing the manufacture of ethanol from biomass and consequently, little effort has been made to eliminate or minimize the small but significant raw material losses which take place in each of the discrete operations involved in the manufacture of ethanol from vegetative sources.

Processes for the continuous fermentation of sugars to provide alcohol are well known (viz., U.S. Pat. Nos. 2,155,134; 2,371,208; 2,967,107; 3,015,612; 3,078,166; 3,093,548; 3,177,005; 3,201,328; 3,207,605; 3,207,606; 3,219,319; 3,234,026; 3,413,124; 3,528,889; 3,575,813; 3,591,454; 3,705,841; 3,737,323; and 3,940,492; "Process Design and Economic Studies of Alternative Fermentation Methods for the Production of Ethanol", Cysewski, et al. *Biotechnology and Bioengineering,* Vol. XX, pp. 1421–1444 (1978)). In a typical continuous fermentation process, a stream of sterile sugar liquor and a quantity of yeast cells are introduced into the first of a battery of fermentation vessels wherein initial fermentation takes place, generally under conditions favoring rapid cell growth. The partial fermentate admixed with yeast cells is continuously withdrawn from the first fermentation vessels wherein fermentation is carried out under conditions favoring the rapid conversion of sugar to ethanol. The yeast in the last fermentation vessel can be recovered by suitable means, e.g., centrifugation or settlement, and recycled. In the various known processes for obtaining fermentable sugar from starch by hydrolysis of the latter, particularly those which employ acid as the hydrolyzing agent, some of the product fermentable sugar will undergo chemical modification to provide oligomers, for example, dimers and/or trimers, which are not readily converted to ethanol using yeasts commonly encountered in the brewing industry. The oligomers which have resisted conversion to ethanol and are therefore present in the product "beer" stream at the conclusion of fermentation are recovered in the distillation bottoms during the process of concentrating the ethanol. Up until now, it has been necessary to re-hydrolyze the recovered oligomers to fermentable sugar and recycle the sugar re-hydrolysate to fermentation when maximum total utilization of raw material for the production of ethanol is desired. However, the additional capital investment needed to provide a plant having the capability to recover, rehydrolyze and recycle the oligomers, and the increased operational complexity and consumption of energy which this capability necessarily entails, have to date militated against the general adoption of the foregoing procedures. Thus, an otherwise valuable raw material for ethanol production, saccharide oligomer, is either being routinely discarded or diverted to uses other than ethanol production.

SUMMARY OF THE INVENTION

In accordance with the present invention, an aqueous solution of fermentable sugar is continuously subjected to fermentation in a series of fermentation vessels employing at least two strains of yeast for the fermentation, one of which provides a relatively high rate of conversion of fermentable sugar to ethanol and the other of which provides a relatively high rate of conversion of oligomers of fermentable sugar to ethanol.

The process herein also contemplates the adjustment of temperature and/or pH in each fermentation vessel as required to maintain optimum fermentation activity therein.

The aqueous ethanol or "beer" containing as much as about 12 weight percent ethanol which is obtained by the foregoing process can be concentrated employing any of the known and conventional techniques and is advantageously concentrated by the anhydrous distillation process disclosed in commonly assigned copending U.S. pat. application Ser. No. 043,189, filed May 29, 1979, now U.S. Pat. No. 4,256,541, issued Mar. 17, 1981. The stillage effluent obtained from the rectifying column employed in the aforesaid anhydrous distillation process contains soluble proteins and amino acids of the original beer feed and provides an excellent source of nutrient for yeast employed in the fermentation process herein.

The use of two or more yeast organisms in the aforestated manner results in a significantly greater degree of direct carbohydrate conversion to ethanol compared to that provided by the use of a single strain of yeast in the current practice. As such, the fermentation process of this invention is particularly well suited for the production of ethanol which is price competitive with ethanol produced from non-vegetative sources.

The term "fermentable sugar" shall be understood to refer to a single fermentable sugar such as glucose (dextrose), fructose, maltose or sucrose but more commonly will be applicable to these and similar fermentable saccharides in admixture. The terms "fermentable sugar oligomer" and "saccharide oligomer" shall be understood to refer to partially repolymerized fermentable sugar, i.e., carbohydrate polymer segments built up from two to five units of fructose, maltose, sucrose, etc, or from three to five units in the case of glucose.

BRIEF DESCRIPTION OF THE DRAWING

The accompanying drawing is a diagrammatic flow sheet illustrative of one embodiment of a continuous ethanol fermentation process in accordance with the present invention.

DESCRIPTION OF THE PREFERRED EMBODIMENTS

Referring to the drawing, a sterile aqueous solution of fermentable sugar from any source containing from about 10 to about 40 weight percent sugar, and preferably from about 15 to about 25 weight percent sugar, is taken from vessel 50 which can be a storage vessel or a saccharification vessel in which the sugar is obtained by the hydrolysis of liquefied starch, and is delivered by pump 51 through line 52 to a first temperature regulated, agitated fermentation vessel 53 provided with pH control and means for introducing nutrients and the small amounts of oxygen conventionally employed for maintaining proper yeast metabolism during fermentation. In the event the sugar solution contains more than 20 weight percent sugar, it is preferable to dilute the solution to about this level of sugar, advantageously with the nitrogen-rich stillage obtained from an ethanol distillation unit. The use of stillage when available possesses the two-fold advantage of recycling nitrogen to the fermentation system which would otherwise be lost upon concentration of the ethanol during distillation, and reducing process water consumption by avoiding water build-up in the still bottoms. In addition to sugar, the foregoing solution may also contain significant amounts of partial starch hydrolysates (e.g., up to about 40 weight percent of the total carbohydrate present) which can be saccharified to fermentable sugar under the influence of the saccharifying enzyme produced by the fermenting yeast and/or added saccharifying enzyme. A pumpable slurry of ethanol producing yeast organisms free of contaminating organisms is conveyed from yeast storage tank 54 by pump 55 through lines 56 and 57 into fermentation vessel 53. The yeast selected for introduction in fermentation vessel 53 is one which provides relatively high rates of ethanol production acting upon a substrate of fermentable sugar. Many yeasts which perform in this manner are known in the brewing industry. *Saccharomyces cerevisiae* is one such yeast and is especially preferred for use herein. The yeast present in fermentation vessels 53 and 67 can be present at a level of from about 2 to about 8 weight percent of the fermentation medium (based on dry weight of yeast) and preferably is present at from about 3 to about 6 weight percent. Once continuous fermentation has started and a steady state has been achieved, excess yeast will form which must continuously or periodically be withdrawn from the fermentation vessel together with the debris of dead yeast cells. The temperature of each fermentation vessel is advantageously regulated at a level which favors maximum ethanol production, i.e., generally from about 68° F. to about 104° F. and preferably from about 86° F. to about 99° F. The pH of each fermentation vessels is similarly regulated and can range from about 3.5 to about 5.5 and preferable from about 4.0 to 4.6. Dilute ethanol produced in fermentation vessel 53 containing a portion of the yeast cells therein is conveyed by pump 58 through line 59 to yeast separator/recovery unit 60 which separates substantially all of the yeast cells from the aqueous ethanol stream. Unit 60 can be a micro-filtration device, centrifuge, etc. Since fermentation is exothermic, a portion of the fermentation medium passing through line 59 is diverted through line 61 into cooler 62 and returned to fermentation vessel 53. The yeast cells recovered in unit 60 are conveyed as a pumpable slurry or "cream" containing from about 5 to about 30 weight percent dry yeast and preferably from about 10 to 25 weight percent dry yeast by pump 63 through lines 64 and 57 into fermentation vessel 53. The ethanol-containing fermentation medium thus freed of the yeast cells is delivered by pump 65 through line 66 into fermentation vessel 67 which is essentially similar to fermentation vessel 53. A pumpable slurry of ethanol-producing yeast organisms essentially free of contaminating organisms is conveyed from yeast storage tank 68 by pump 69 through lines 70 and 71 into fermentation vessel 67. The yeast selected for introduction in fermentation vessel 67 is one which is especially effective for converting saccharide oligomers to ethanol, several of which are known in the art. *Saccharomyces carlsbergensis* and *Saccharomyces cerevisiae var. ellipsoideus* are illustrative of yeasts which can be advantageously used in fermentation vessel 67. The dilute aqueous ethanol (approximately 10 to 12 weight percent ethanol) containing yeast cells is withdrawn from fermentation vessel 67 and conveyed by pump 72 through line 73 to yeast separator/recovery unit 74. A portion of the fermentation medium passing through line 73 is diverted through line 75 into cooler 76 and returned to fermentation vessel 67. The yeast cells recovered in unit 74 are conveyed as a pumpable slurry (similar in fluid characteristics to the yeast slurry recovered from unit 60) by pump 77 through lines 78 and 71 to fermentation vessel 67. The cell-free ethanol solution from yeast separator/recovery unit 74 is delivered by pump 79 through line 80 directly to an ethanol concentration unit, e.g., anhydrous distillation apparatus, and/or to a storage facility. It is also within the scope of this invention to employ both types of yeast herein in such fermentation vessel with only one yeast separation/recovery unit (receiving the fermentation medium from the last fermentation vessel in the series) being provided. Metabolically evolved carbon dioxide gas containing ethanol is conveyed from each of fermentation vessels 53 and 67 through common line 81 and by means of blower 82 is introduced into the bottom of ethanol absorption unit 83. Water at ambient temperature entering the top of the absorption unit through line 84 and flowing downwardly, absorbs substantially all of the ethanol vapor rising through the unit. The aqueous solution of ethanol withdrawn from the base of ethanol absorption unit 83 through line 85 is conveyed to line 80 where it is combined with the bulk of the flow from the last fermenter. Vent gases are discharged from ethanol absorption unit 83 through atmospheric vent line 86.

What is claimed is:

1. A process for the production of ethanol by continuous fermentation which comprises carrying out fermentation upon an aqueous solution of fermentable sugar and fermentable sugar oligomer in a series of fermentation vessels, the fermentation employing at least two different strains of ethanol-producing yeast, one of which provides a relatively high rate of conversion of fermentable sugar to ethanol and the other of which provides a relatively high rate of conversion of fermentable sugar oligomer to ethanol, each of said strains of yeast being separately employed in its own fermentation vessel from which said yeast is separately recovered therefrom and recycled thereto.

2. The process of claim 1 wherein the aqueous solution of fermentable sugar contains partial starch hydrolysate in an amount of up to about 40 weight percent of fthe total carbohydrate present, the partial starch hydrolysate undergoing saccharification to fermentable sugar under the influence of saccharifying enzyme produced by the yeast and/or added saccharifying enzyme.

3. The process of claim 1 wherein the strain of yeast which provides a relatively high rate of conversion of fermentable sugar to ethanol is *Saccharomyces cerevisiae*.

4. The process of claim 1 wherein the strain of yeast which provides a relatively high rate of conversion of fermentable sugar oligomer to ethanol is *Saccharomyces carlsbergensis* or *Saccharomyces cerevisiae var. ellipsoideus*.

5. The process of claim 1 wherein ethanol contained in the carbon dioxide gas evolved during fermentation is recovered.

6. The process of claim 1 wherein from 2 to 8 weight percent of yeast calculated on a dry yeast basis is present in each fermentation vessel.

7. The process of claim 6 wherein from 3 to 6 weight percent of yeast calculated on a dry yeast basis is present in each fermentation vessel.

8. The process of claim 1 wherein the aqueous solution of fermentable sugar contains from about 10 to about 40 weight percent sugar.

9. The process of claim 8 wherein the aqueous solution of fermentable sugar contains from about 15 to 25 weight percent sugar.

* * * * *